United States Patent [19]

Oshiyama et al.

[11] Patent Number: 5,000,764
[45] Date of Patent: Mar. 19, 1991

[54] BLOOD STORAGE CONTAINER

[75] Inventors: Hiroaki Oshiyama; Takeshi Kuroo, both of Fuji, Japan

[73] Assignee: Terumo Kabushiki Kaisha, Tokyo, Japan

[21] Appl. No.: 393,518

[22] Filed: Aug. 14, 1989

[30] Foreign Application Priority Data

Aug. 26, 1988 [JP] Japan .................................. 63-211645

[51] Int. Cl.$^5$ ............................................. B01D 53/00
[52] U.S. Cl. ......................................... 55/159; 55/487; 210/188; 210/436
[58] Field of Search ................... 55/159, 487; 210/188, 210/436, 489, 500.24, 500.35; 422/45, 46

[56] References Cited

U.S. PATENT DOCUMENTS

| 3,507,395 | 12/1987 | Bentley . | |
|---|---|---|---|
| 3,650,093 | 3/1972 | Rosenberg et al. | 55/159 |
| 3,701,433 | 10/1972 | Krakauer et al. | 210/436 |
| 4,303,530 | 12/1981 | Shah et al. | 210/489 X |
| 4,568,367 | 2/1986 | Gremel et al. . | |
| 4,572,724 | 2/1986 | Rosenberg | 55/159 |
| 4,642,089 | 2/1987 | Zupkas et al. . | |
| 4,690,762 | 9/1987 | Katsura . | |
| 4,704,203 | 11/1987 | Reed . | |
| 4,705,497 | 11/1987 | Shitaokoshi et al. . | |
| 4,737,139 | 4/1988 | Zupkas et al. . | |
| 4,743,371 | 5/1988 | Servas et al. . | |

FOREIGN PATENT DOCUMENTS

| 2844073 | 4/1980 | Fed. Rep. of Germany . |
| 2443268 | 7/1980 | France . |
| 2600537 | 12/1987 | France . |
| 59-57661 | 4/1984 | Japan . |
| 62-46187 | 10/1987 | Japan . |
| 62-258671 | 11/1987 | Japan . |
| 62-258673 | 11/1987 | Japan . |
| 63-102764 | 5/1988 | Japan . |

Primary Examiner—Charles Hart
Attorney, Agent, or Firm—Frishauf, Holtz, Goodman & Woodward

[57] ABSTRACT

A blood storage container includes a blood storage chamber having a blood outlet port, a blood inlet chamber disposed upstream of the blood storage chamber with respect to a direction in which blood to be stored flows, a blood debubblizer for debubblizing the blood, the blood debubblizer being disposed between the blood inlet chamber and the blood storage chamber, and an air bubble stop unit for preventing air bubbles in the blood from flowing therethrough, the air bubble stop unit being disposed downstream of the blood debubblizer. The air bubble stop unit has mesh screens of different mesh sizes which are supported in a frame that is detachably disposed in the blood storage chamber.

9 Claims, 5 Drawing Sheets

BLOOD STORAGE CONTAINER

BACKGROUND OF THE INVENTION

The present invention relates to a blood storage container, and more particularly to a blood storage container for use in an open-type pump oxygenator circuit or the like.

When a surgical operation is effected on the chest of a patient, an oxygenator is often used recently in connection with an extracorporeal blood circulation circuit in bypassing relation to the lung of the patient, and carbon dioxide is removed from the blood of the patient and fresh oxygen is added to the blood by the oxygenator.

The extracorporeal blood circulation circuit includes a blood storage container for temporarily storing the blood so that air bubbles produced during the circulation of the blood will be removed from the blood, or the rate of circulation of the blood will be prevented from dropping due to the bending of a tube of the extracorporeal blood circulation circuit. Blood storage containers now in use in the arm are roughly classified into a closed-type soft bag container which is made of a soft material and stores the blood in a hermetically sealed condition, and an open-type hard shell container which is made of a hard material and stores the blood in an open or vented condition. The soft bag container is advantageous in that it has no blood-air interface, but disadvantageous in that it cannot hold a large amount of blood and cannot give an exact indication of how much blood is stored therein.

The hard shell container can store a large amount of blood and allows the user to know the exact amount of blood stored therein. Other advantages of the hard shell container are that it can easily be united with an oxygenator thus permitting an extracorporeal blood circulation circuit to be arranged with ease, and also the blood can easily be debubblized when the extracorporeal blood circulation circuit is set up and primed. Japanese Laid-Open patent Publication No. 59-57661, for example, proposes a hard shell blood storage container which utilizes these advantages.

The conventional blood storage container which is united with an oxygenator, however, has no mechanism for removing air bubbles from the blood that ingresses into the container. Air bubbles must be removed from the blood in order to prevent the patient from suffering embolism. Therefore, the extracorporeal blood circulation circuit should be provided with a debubblizing mechanism in another region than the blood storage container.

It is nevertheless preferable to provide the blood storage container with a debubblizer for removing air bubbles from the stored blood, so that the extracorporeal blood circulation circuit will be made compact as a whole. Japanese Laid-Open patent Publication No. 62-258671 discloses a blood storage container which incorporates a blood debubblizer therein. The disclosed blood debubblizer comprises a foamed body integral with the blood storage container. The foamed body is of a hydrophobic nature to allow air bubbles in the blood to grow and be removed with a view to protecting the patient from embolism.

The foamed body positioned in the blood storage container is effective in removing relatively large air bubbles from the blood which has entered from a blood inlet into the foamed body. However, some very small air bubbles in the blood may pass through the foamed body and remain in the blood which returns into the body of the patient. When this happens, the patient may be afflicted with embolism owing to those very small air bubbles that remain trapped in the blood.

SUMMARY OF THE INVENTION

It is therefore a principal object of the present invention to provide a blood storage container for use with an extracorporeal blood circulation apparatus or the like for removing tiny air bubbles and also foreign matter substantially completely from the blood stored in the container.

Another object of the present invention is to provide a blood storage container comprising a blood storage chamber having a blood outlet port, a blood inlet chamber disposed upstream of the blood storage chamber with respect to a direction in which blood to be stored flows, blood debubblizing means for debubblizing the blood, the blood debubblizing means being disposed between the blood inlet chamber and the blood storage chamber, and air bubble stop means for preventing air bubbles in the blood from flowing therethrough, the air bubble stop means being disposed downstream of the blood debubblizing means.

Still another object of the present invention is to provide the blood storage container wherein the air bubble stop means comprises mesh screens.

Yet another object of the present invention is to provide the blood storage container wherein the mesh screens include a mesh screen of larger mesh size and a mesh screen of smaller mesh size, the air bubble stop means including a frame in which the mesh screens are supported.

Yet still another object of the present invention is to provide the blood storage container wherein the mesh screen of larger mesh size is positioned upwardly of the mesh screen of smaller mesh size.

A further object of the present invention is to provide the blood storage container wherein the mesh screen of smaller mesh size is positioned upwardly of the mesh screen of larger mesh size.

A still further object of the present invention is to provide the blood storage container wherein the mesh screens have mesh sizes ranging from 50 to 300 mesh size.

A yet further object of the present invention is to provide the blood storage container wherein the mesh screen of larger mesh size has a mesh size ranging from 50 to 300, preferably from 75 to 250.

A yet still further object of the present invention is to provide the blood storage container wherein the mesh screen of larger mesh size has a mesh size ranging from 50 to 175, preferably from 75 to 150.

Another object of the present invention is to provide the blood storage container wherein the mesh screens are detachably mounted in the blood storage chamber.

Still another object of the present invention is to provide the blood storage container wherein the mesh screens are treated such that they are hydrophilic.

Yet another object of the present invention is to provide the blood storage container wherein the mesh screens are coated with silicone.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figure 1:
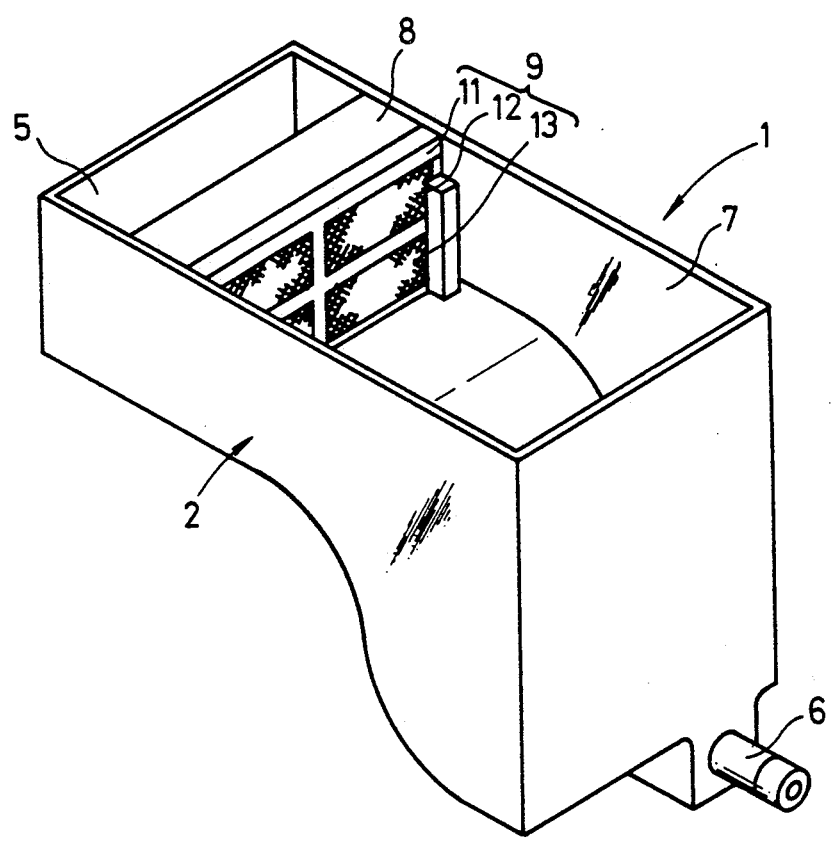
FIG. 1 is a perspective view of a blood storage container according to the present invention.

FIG. 1 shows a blood storage container 1 according to the present invention which is to be incorporated in an extracorporeal blood circulation apparatus (described later on). The blood storage container 1 is of the hard shell type to be assembled in the extracorporeal blood circulation apparatus which includes an oxygenator. The blood storage container 1 basically comprises a container casing 2 and a cover 3 (FIG. 4) for closing the upper opening of the container casing 2. The container casing 2 is made of a hard material such as polyvinyl chloride, polystyrene, polycarbonate, or the like. The container casing 2 should preferably be transparent so as to allow the user to visually observe the blood stored in the container casing 2.

Figure 4:
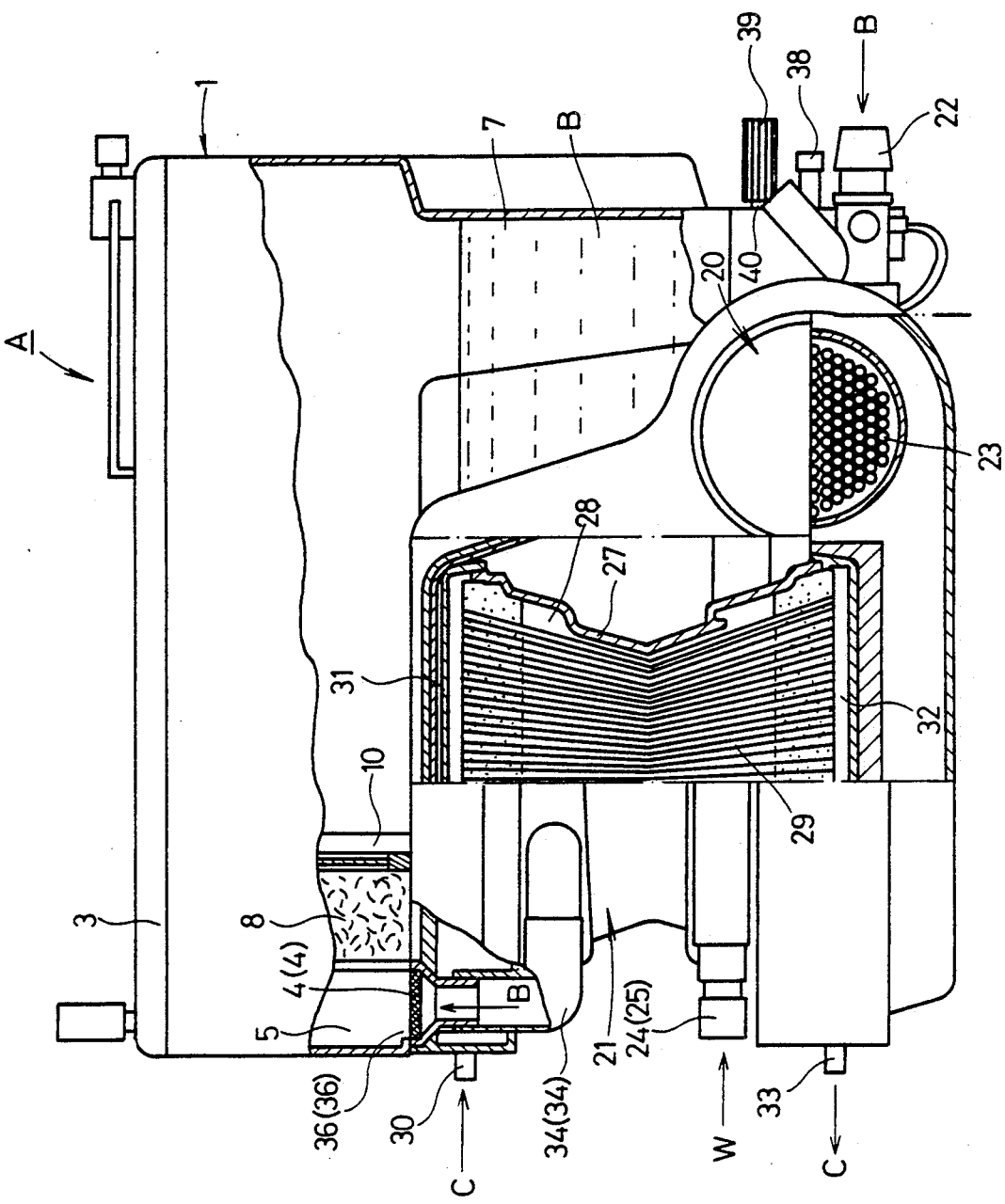
FIG. 4 is a side elevational view, partly in cross section, of an extracorporeal blood circulation apparatus in which the blood storage container of the present invention is incorporated.
Figure 5:
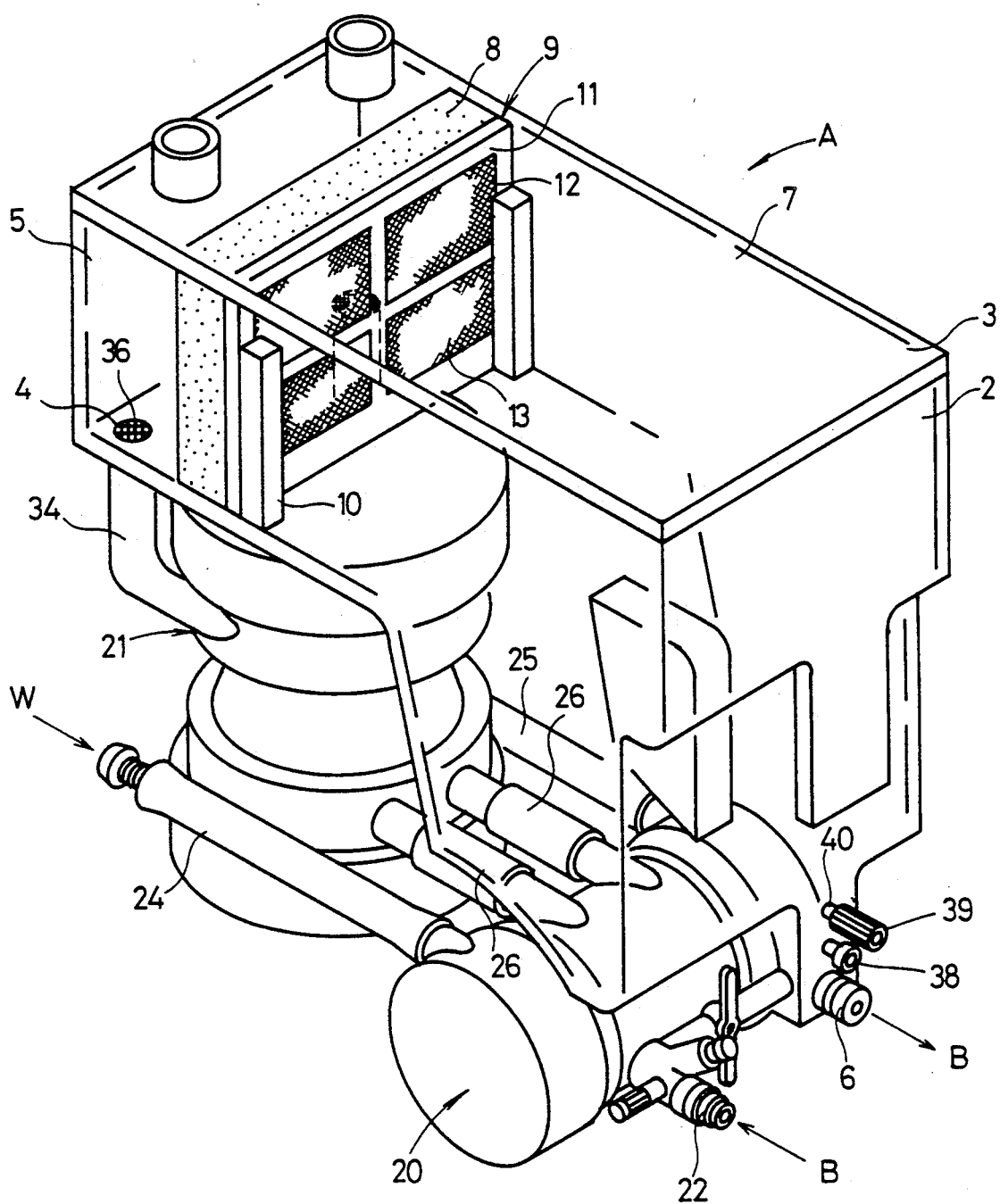
FIG. 5 is a schematic perspective view of the extracorporeal blood circulation apparatus shown in FIG. 4.

As shown in FIGS. 4 and 5, the container casing 2 has a pair of blood inlet ports 4 defined in the bottom of one end thereof, a blood inlet chamber 5 communicating with the blood inlet ports 4 and having a bottom which is substantially at the same level as the blood inlet ports 4, and a blood storage chamber 7 communicating with the blood inlet chamber 5 and having a bottom extending from the blood inlet chamber 5 downwardly along a curved surface toward the other end of the blood storage chamber 7 remote from the blood inlet chamber 5, the blood storage chamber 7 having a blood outlet port 6 in a lower portion thereof. A blood debubblizer 8 is positioned between the blood storage chamber 7 and the blood inlet chamber 5. An air bubble stop unit 9 is detachably disposed on a downstream side of the blood debubblizer 8 which faces the blood storage chamber 7. The blood debubblizer 8 and the air bubble stop unit 9 are prevented from being displaced toward the blood outlet port 6 by means of locking members 10 vertically attached to the inner surfaces of side walls of the blood storage chamber 7. When blood containing air bubbles flows into the blood inlet chamber 5, the blood debubblizer 8 removes the air bubbles from the blood as it flows therethrough, and hence supplies the debubblized blood into the blood storage chamber 7. The blood debubblizer 8 is preferably in the form of a three-dimensional a foamed body which is of a hydrophobic nature to allow air bubbles in the blood to grow and be removed.

The air bubble stop unit 9 may be made of any of various materials insofar as they allow liquids to flow therethrough. However, the resistance to liquid flows of the material of the air bubble stop unit 9 should be small enough not to develop any appreciable pressure loss in a blood flow upon contact with the blood flow through the air bubble stop unit 9.

Figure 2:
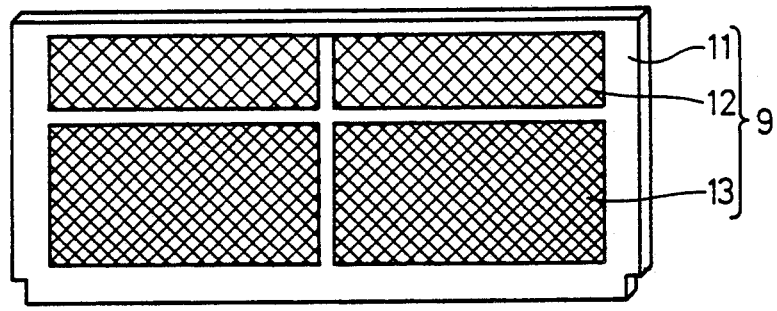
FIG. 2 is a perspective view of an air bubble stop unit of the blood storage container.

As shown in FIG. 2, the air bubble stop unit 9 has a frame 11 including a crisscross inner frame member, a mesh screen 12 of a larger mesh size disposed in an upper portion of the frame 11, and a mesh screen 13 of a smaller mesh size disposed in a lower portion of the frame 11. The mesh sizes of the mesh screens 12, 13 should be in the range of from 50 to 300 mesh, and more preferably in the range of from 75 to 250 mesh as a whole.

More specifically, the mesh size of the mesh screen 12 should range from 50 to 300 mesh, and preferably from 50 to 175 mesh, and more preferably of 100 mesh/inch, and the mesh size of the mesh screen 13 should range from 125 to 300, and more preferably from 150 to 250 mesh. Each of the mesh screens 12, 13 is of a plain weave woven of polyester filaments. The mesh screen 12 should preferably have a filament diameter of 55 $\mu$m and a thickness of 95 $\mu$m and the mesh screen 13 should preferably have a filament diameter of 45 $\mu$m and a thickness of 75 $\mu$m. In the embodiment shown in FIG. 2, the width between adjacent filaments of the mesh screen 12, i.e., the mesh opening, is 199 $\mu$m with an opening area of 61%, whereas the mesh opening of the mesh screen 13 is 124 $\mu$m with an opening area of 54%. The material of the mesh screens 12, 13 should not activate the blood constituents upon contact with the blood. Examples of the material of the mesh screens 12, 13 include polyvinyl chloride, polyethylene, polypropylene, polyester, polycarbonate, or the like. It may be preferable to coat the filaments of the mesh screens 12, 13 with silicone resin because the silicone coating will vary the surface tension to permit air bubbles attached to the filaments to glow and be removed from the blood.

The mesh screens 12, 13 may be coated with a polymer so that they will become hydrophilic. Generally, mesh screens are hydrophobic and do not allow blood to flow easily therethrough particularly during an initial phase of usage thereof. However, by making the mesh screens 12, 13 hydrophilic, they allow blood to flow easily therethrough even during an initial period of usage thereof. The polymer to be coated on the mesh screens 12, 13 to render them hydrophilic should contain hydroxymethylmethacrylate (HEMA) and methylmethacrylate (MMA). The desired hydrophilic nature is obtained by a polymer containing MMA and HEMA at proportions of 92 and 8, respectively.

As described above, the mesh screens 12, 13 may be coated with either silicone so as to be hydrophobic, or a polymer so as to be hydrophilic. However, it is most preferable to coat the blood debubblizer 8 with silicone so as to make it hydrophobic and also to make the air bubble stop unit 9 hydrophilic. By doing so, the hydrophobic nature of the blood debubblizer 8 is promoted to positively attract air bubbles contained in the blood, thus allowing the air bubbles to grow and be removed from the blood. The air bubble stop unit 9 which is rendered hydrophilic can easily catch air bubbles with the very fine mesh screens. The blood flows very smoothly through the blood debubblizer 8 and the air bubble stop unit 9 because the blood storage container 1 is used with the oxygenator which is of the head perfusion type.

The mesh screen 12 of larger mesh size may be disposed in the lower portion of the frame 9, and the mesh screen 13 of smaller mesh size may be disposed in the upper portion of the frame 11. Alternatively, the mesh screen 13 of smaller mesh size may be disposed in each of the upper and lower portions of the frame 11. If the mesh screen 12 of larger mesh size is disposed in the lower portion of the frame 11 and the mesh screen 13 of smaller mesh size is disposed in the upper portion of the frame 11, then since air bubbles contained in the blood move up when the blood flows through the mesh screens 12, 13, the air bubbles are removed by the upper mesh screen 13 of smaller mesh size, whereas the pressure loss of the blood flowing through the lower mesh screen 12 is prevented from being lowered by the mesh screen 12 which is of larger mesh size.

Figure 3:
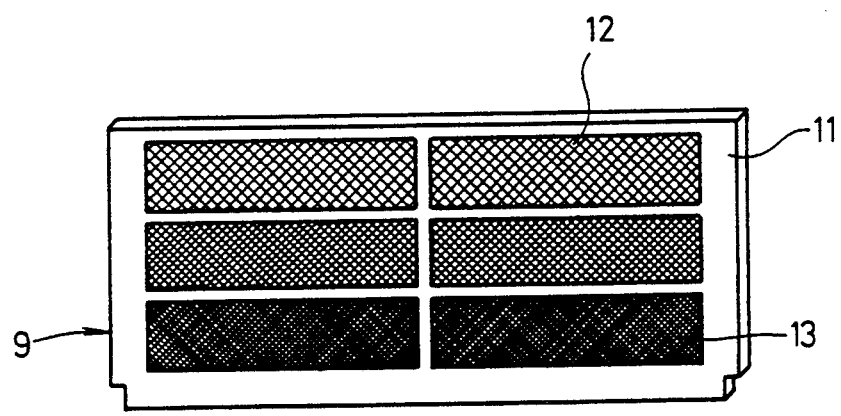
FIG. 3 is a perspective view of an air bubble stop unit according to another embodiment of the present invention.

Mesh screens for removing air bubbles and foreign matter from the blood may include a mesh screen 13 of smaller mesh size, a mesh screen 12 of larger mesh size, and a mesh screen of intermediate mesh size, which are positioned in juxtaposed relation in a frame 11, as shown in FIG. 3.

The blood storage container 1 thus constructed is used with an extracorporeal blood circulation apparatus A illustrated in FIGS. 4 and 5.

The extracorporeal blood circulation apparatus A comprises a heat exchanger 20 and an oxygenator 21 which is coupled to the blood storage container 1 of the present invention.

Blood B flows from the superior and inferior vena cava of a patient (not shown) into a blood support port 22 through medical tubes (not shown). The blood B is then supplied to the oxygenator 21 through gaps between tubes 23 stored in the heat exchanger 20. At this time, water W maintained at a predetermined temperature flows in the tubes 23 through water ports 24, 25. Therefore, the blood B flows through the gaps between the tubes 23 is heated or cooled to the predetermined temperature by the water W.

The blood B then flows from the heat exchanger 20 into the oxygenator 21 through joint tubes 26. Oxygen is added to and carbon dioxide is removed from the blood B in a gas exchange chamber 28 surrounded by a housing 27 of the oxygenator 21. More specifically, a bundle of hollow filamentary membranes 29 which is disposed in the chamber 28 is supplied with a gas C containing oxygen from a gas inlet port 30 through a gas supply chamber 31. Therefore, oxygen and carbon dioxide are exchanged in the blood B through the hollow filamentary membranes 29. A gas C containing carbon dioxide is discharged from a gas discharge chamber 32 through a gas outlet port 33.

The blood B with oxygen added thereto by the oxygenator 21 is directed through joint tubes 34 and the blood inlet ports 4 into the blood inlet chamber 5 of the blood storage container 1. At this time, the flow of the blood B is smoothed by mesh screens 36 fitted in the blood inlet ports 4. Relatively large air bubbles are then removed from the blood B by the blood debubblizer 8.

Very small or minute air bubbles which have not removed from the blood B by the blood debubblizer 8 are then trapped and removed by the air bubble stop unit 9. Therefore, the blood B which is completely free of air bubbles is sent to the blood storage unit 7. Inasmuch as the mesh screen 12 of large mesh size is disposed in the upper portion of the frame 11 of the air bubble stop unit 9 and the mesh screen 13 of small mesh size is disposed in the lower portion of the frame 11, even if the mesh screen 13 happens to be clogged by small air bubbles or foreign matter that may have been contained in the blood B, the blood B is directed toward the mesh screen 12 positioned above the mesh screen 13. Therefore, the blood B is prevented from flowing through the air bubble stop unit 9.

The blood outlet port 6, a BCP port 38 for protecting the heart muscles of the patient, and a port 40 which receives a thermistor probe 39 are defined in the lower portion of the blood storage container 1 near the heat exchanger 20, these ports being successively arranged upwardly in the order named. The blood B stored in the blood storage container 1 will be supplied to the aorta of the patient by means of a pump (not shown) communicating with the blood outlet port 6.

As described above, the air bubble stop unit 9 composed of the mesh screens is disposed downstream of the blood debubblizer 8. Even if the blood that has flowed into the blood inlet chamber 5 contains air bubbles, relatively large air bubbles are trapped and removed by the blood debubblizer 8 as the blood flows therethrough. Minute air bubbles which are not removed by the blood debubblizer 8 and hence remain in the blood are then trapped by the air bubble stop unit 9. Therefore, any blood which contains air bubbles is not returned from the blood storage container 1 to the patient, and the patient is prevented from suffering embolism. Since the mesh screens of the air bubble stop unit 9 have mesh sizes ranging from 50 to 300 mesh, minutes air bubbles which may have been contained in the blood having passed through the blood debubblizer 8 can completely be removed from the blood without developing a substantial pressure loss in the blood.

Since the mesh screens of the air bubble stop unit 9 have different mesh sizes, even if the mesh screen of smaller mesh size are clogged with air bubbles, foreign matter, or the like, the blood is allowed to flow through the mesh screen of larger mesh size. Therefore, the air bubble stop unit does not interrupt the flow of the blood therethrough. It is possible to remove minute air bubbles mainly with the mesh screen of smaller mesh size, and to minimize a pressure loss in the blood with the mesh screen of larger mesh size. Accordingly, the blood can flow at all times without an obstruction, while at the same time minute air bubbles can be completely removed from the blood and any pressure loss in the blood is held at a minimum.

The air bubble stop unit 9 may be installed inversely so that the mesh screens 12, 13 will be positioned upside down.

Although certain preferred embodiments have been shown and described, it should be understood that many changes and modifications may be made therein without departing from the scope of the appended claims.

What is claimed is:

1. A blood storage container, comprising:
a blood storage chamber having a blood outlet port;
a blood inlet chamber disposed upstream of said blood storage chamber with respect to a direction in which blood to be stored flows;
blood debubblizing means for debubblizing the blood, said blood debubblizing means being disposed between said blood inlet chamber and said blood storage chamber; and
air bubble stop means comprising a plurality of mesh screens for preventing air bubbles in the blood from flowing therethrough, said air bubble stop means being disposed downstream of said blood debubblizing means and between said blood inlet chamber and said blood storage chamber, said blood debubblizing means and said air bubble stop means being disposed substantially at the same level;

wherein said plurality of mesh screens includes a mesh screen of a larger mesh size and a mesh screen of a smaller mesh size, said mesh screen of a larger mesh size being disposed vertically above said mesh screen of a smaller mesh size.

2. A blood storage container according to claim 1, said air bubble stop means including a frame in which said mesh screens are supported.

3. A blood storage container according to claim 2, wherein said mesh screens have mesh sizes ranging from 50 to 300 mesh size.

4. A blood storage container according to claim 3, wherein said mesh screen of smaller mesh size has a mesh size ranging from 125 to 300, preferably from 150 to 250.

5. A blood storage container according to claim 3, wherein said mesh screen of larger mesh size has a mesh size ranging from 50 to 175, preferably from 75 to 150.

6. A blood storage container according to claim 2, wherein said mesh screens are detachably mounted in said blood storage chamber.

7. A blood storage container according to claim 2, wherein said mesh screens are treated such that they are hydrophilic.

8. A blood storage container according to claim 2, wherein said mesh screens are coated with silicone.

9. A blood storage container, comprising:
a blood storage chamber having a blood outlet port;
a blood inlet chamber disposed upstream of said blood storage chamber with respect to a direction in which blood to be stored flows;
blood debubblizing means for debubblizing the blood, said blood debubblizing means being disposed between said blood inlet chamber and said blood storage chamber; and
air bubble stop means comprising a plurality of mesh screens for preventing air bubbles in the blood from flowing therethrough, said air bubble stop means being disposed downstream of said blood debubblizing means and between said blood inlet chamber and said blood storage chamber, said blood debubblizing means and said air bubble stop means being disposed substantially at the same level;
wherein said plurality of mesh screens includes a mesh screen of a larger mesh size and a mesh screen of a smaller mesh size, said mesh screen of a smaller mesh size being disposed vertically above said mesh screen of a larger mesh size.

* * * * *